(12) United States Patent
Dumont et al.

(10) Patent No.: US 9,567,290 B2
(45) Date of Patent: Feb. 14, 2017

(54) ESTERS OF N-ACYL DERIVATIVES OF AMINO ACIDS AND DIOLS, METHOD FOR PREPARING SAME, AND USE THEREOF IN COSMETICS AND AS A DRUG

(71) Applicant: SOCIETE D'EXPLOITATION DE PRODUITS POUR LES INDUSTRIES CHIMIQUES SEPPIC, Paris (FR)

(72) Inventors: Sandy Dumont, Caucalieres (FR); Jerome Guilbot, Castres (FR); Stephanie Garcel, Castres (FR); Laetitia Cattuzzato, Castres (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 0 days.

(21) Appl. No.: 14/350,635

(22) PCT Filed: Oct. 12, 2012

(86) PCT No.: PCT/FR2012/052324
§ 371 (c)(1),
(2) Date: Apr. 9, 2014

(87) PCT Pub. No.: WO2013/060964
PCT Pub. Date: May 2, 2013

(65) Prior Publication Data
US 2014/0288144 A1  Sep. 25, 2014

(30) Foreign Application Priority Data

Oct. 27, 2011 (FR) ..................... 11 59762

(51) Int. Cl.
| | | |
|---|---|---|
| C07C 233/47 | (2006.01) | |
| C07C 233/49 | (2006.01) | |
| C07D 207/16 | (2006.01) | |
| A61K 8/49 | (2006.01) | |
| A61Q 19/00 | (2006.01) | |
| A61K 31/401 | (2006.01) | |
| A61K 8/44 | (2006.01) | |
| A61Q 19/08 | (2006.01) | |
| A61K 8/42 | (2006.01) | |
| A61Q 19/02 | (2006.01) | |
| C07C 231/12 | (2006.01) | |

(52) U.S. Cl.
CPC .............. *C07C 233/47* (2013.01); *A61K 8/42* (2013.01); *A61K 8/44* (2013.01); *A61K 8/4913* (2013.01); *A61K 31/401* (2013.01); *A61Q 19/00* (2013.01); *A61Q 19/02* (2013.01); *A61Q 19/08* (2013.01); *C07C 231/12* (2013.01); *C07C 233/49* (2013.01); *C07D 207/16* (2013.01)

(58) Field of Classification Search
CPC .... C07D 207/16; C07C 233/47; C07C 233/49
See application file for complete search history.

(56) References Cited

U.S. PATENT DOCUMENTS

| | | | |
|---|---|---|---|
| 5,888,482 A | 3/1999 | Amalric et al. | |
| 5,958,431 A | 9/1999 | Brancq et al. | |
| 6,245,821 B1 | 6/2001 | Bulcourt et al. | |
| 6,268,400 B1 | 7/2001 | Amalric et al. | |
| 6,353,034 B1 | 3/2002 | Amalric et al. | |
| 6,464,993 B1 | 10/2002 | Milius et al. | |
| 6,488,946 B1 | 12/2002 | Milius et al. | |
| 6,667,396 B2 | 12/2003 | Milius et al. | |

FOREIGN PATENT DOCUMENTS

| | | |
|---|---|---|
| EP | 0839515 | 10/1997 |
| EP | 1216696 | 12/2001 |
| FR | 2 668 080 | 4/1992 |
| FR | 2 734 496 | 11/1996 |
| FR | 2 756 195 | 5/1998 |
| FR | 2 762 317 | 10/1998 |
| FR | 2 784 680 | 4/2000 |
| FR | 2 784 904 | 4/2000 |
| FR | 2 790 977 | 9/2000 |
| FR | 2 791 565 | 10/2000 |

(Continued)

OTHER PUBLICATIONS

Shibata, et al. Document No. 156:288947, retrieved from CAPLUS, entered in STN on Feb. 16, 2012.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http:llwww.cnn.com120031HEALTHlconditionslO91241alzheimers.drug.aplindexhtml>.*
International Search Report dated Dec. 6, 2012 in corresponding PCT application.

(Continued)

*Primary Examiner* — Shawquia Jackson
(74) *Attorney, Agent, or Firm* — Young & Thompson

(57) ABSTRACT

A compound of formula (I): R'—O-A-O—R", in which R' and R" are a hydrogen atom or a monovalent radical of formula (IIa), or a monovalent radical of formula (IIb), it being understood that at least one of the radicals R' or R" is not a hydrogen atom and that, when none of the radicals R' and R" is a hydrogen atom, R' and R" are identical, and in which A is a divalent radical of formula (III): —CH(X1)-[C(X2)(X3)]p-CH(X4) in which X1, X2, X3 and X4 are identical or different and are either a hydrogen atom or a methyl radical or an ethyl radical, and p is an integer greater than or equal to 1 and less than or equal to 6. Also the method for preparing the compound of formula (I) and to the use thereof in cosmetics and as a drug.

19 Claims, No Drawings

(56) References Cited

FOREIGN PATENT DOCUMENTS

| FR | 2 804 432 | 8/2001 |
|---|---|---|
| FR | 2 807 435 | 10/2001 |
| FR | 2883171 | 9/2006 |
| JP | 2000-229921 | 8/2000 |
| JP | 2002 167313 | 6/2002 |
| JP | 2012 031216 | 2/2012 |
| WO | 99/59958 | 11/1999 |
| WO | 2008/035152 | 3/2008 |
| WO | 2008/141296 | 11/2008 |
| WO | 2010/034917 | 4/2010 |

OTHER PUBLICATIONS

French Search Report dated Jul. 5, 2012 in corresponding French priority application.
Prabhudesai A. V. et al: "Synthesis of mixed diesters of ethanediol with N-acyl amino acids and fatty acids", Chemistry and Physics of Lipids, Limerick, IR, vol. 22, No. 1, Aug. 1, 1978 (Aug. 1, 1978), pp. 71-77, XP023389034, ISSN: 0009-3084.

* cited by examiner

ESTERS OF N-ACYL DERIVATIVES OF AMINO ACIDS AND DIOLS, METHOD FOR PREPARING SAME, AND USE THEREOF IN COSMETICS AND AS A DRUG

The present invention concerns novel chemical products, and novel chemical compositions, intended for preventing and/or treating visible signs of malfunctioning of the venous system and/or alternation in the vascular permeability of the human skin.

The human skin constitutes the first image offered to the gaze of other people, and consequently improving the appearance thereof is a constant subject of preoccupation for human beings. The skin is the reflection of a state of wellbeing, often associated with youth, and on the other hand a state of a fatigue and/or aging.

Good functioning of blood microcirculation constitutes one of the essential factors that govern good cutaneous aesthetic state. The phenomenon of aging results in particular in a reduction in the number, size and functionality of the dermal vessels that ensure functioning of the blood microcirculation, and have a tendency to become less numerous and more fragile.

This rarefaction of the subcutaneous capillary vessels causes lower oxygenation of the skin and a reduction in the contribution of nutriments (trace elements and vitamins), which results, in an aged human being in chronic facial pallor (bibliographic references (1), (2) and (3). Likewise, any malfunctioning of the venous system, which is characterised by a slowing of blood circulation, produces the same phenomenon of insufficient oxygenation of the tissue known as hypoxia.

The concept of vascular permeability describes the role played by small blood vessels (arterioles, venules or microvessels) in affording a functional barrier between the blood circulating in said small blood vessels and the tissues, and more particularly the cutaneous tissues. When vascular permeability is altered under the effect of aging and/or inflammatory phenomena and/or stress of external origin, the tissues then in a situation of hypoxia are inflamed, which manifests in the appearance of phenomena of exacerbated red blotches, which may go as far as the formation of oedemata on the skin area concerned. The vessels may moreover dilate or even rupture, causing the formation of telangiectases.

The endothelium is a tissue the prime function of which is to contain the blood in the blood vessels, enabling the exchange of nutritive substances with the internal environment. It is formed by the endothelial cells and muscular cells, which act as molecular "filters" to enable this exchange of nutritive substances, the function of which is to control blood coagulation and the vasomotricity of the individual. The humoral mediators, hormones, cytokines or growth factors constitute biochemical constraints that act on the activation of the endothelial cells. The endothelial cells are sensitive to oxidative stress, caused by an increased presence of oxygenated derivatives, such as for example superoxide ions, hydrogen peroxides and hydroxyl radicals, which exceed the regulatory capacities of the natural antioxidant system (superoxydismutase, catalase, etc.), which results in particular in a reduction in oxygen available in the endothelial cells, namely a phenomenon of hypoxia of said endothelial cells, and consequently a reduction in the production of adenine triphosphate (ATP) in said endothelial cells.

According to the literature (bibliographic reference (4) Janssens "Effect of venotropic drugs on the respiratory activity of isolate mitochondria and in endothelial cells", in British Journal of Pharmacology (2000) 130, 1513-1524), venous insufficiencies resulting from malfunctioning of the venous system and/or alteration to the vascular permeability, which result in a reduction in the arterial blood contribution to an organ (or ischemia), which causes essentially a reduction in the oxygenation of the tissues of the organ below its requirements in order to put it in a situation of hypoxia and consequently a reduction in the production of ATP by the endothelial cells.

According to the organisation of the endothelial cells in the organs, the endothelium fulfils a specific function of said organ. Because of this, when they are subjected to a mechanical or biochemical stress, the endothelial cells generate responses to the stimuli of various natures (exposure to ultraviolet radiation, high variation in temperature and/or humidity, pollution, etc.), which have different macroscopic consequences. Thus malfunctioning of the venous system and/or alteration to vascular permeability, caused and/or exacerbated by mechanical and/or biochemical stresses, may result in a situation of hypoxia in the region of the contour of the eye manifesting in the appearance of oedema of non-inflammatory character, and in particular the appearance of dark circles and/or bags under the eyes, or at the lower limbs, or in the appearance of sensations of heaviness of the limbs resulting in particular in swelling of the calf and/or feet and/or ankles.

The region of the contour of the eye is characterised by a dense innervation and by a fine skin, with a low skin lipid content, then revealing itself to be very sensitive to external stresses (state of fatigue, lack of sleep, exposure to UV, tobacco, alcohol, etc.) and to various mechanical and biochemical stresses. Malfunctioning of the venous system and/or alteration to the vascular permeability that result in a vasodilation or a congestion of the blood capillaries in this particular area of the contour of the eye are also more visible because of the thinness of the skin. When vasodilation or congestion of the blood capillaries present under the eyes persists, these phenomena give rise to sensations of persistent discomfort and cause the appearance of dark circles and/or bags under the eyes, which then have an unaesthetic character. Skin aging also results in a reduction in the number, size and functionality of the dermal vessels, which causes a reduction in the nutritional take-up and in the glow of the complexion. These phenomena are also reinforced by a slowed lymphatic circulation in this area of the contour of the eye.

With regard to the phenomenon or sensation of heaviness in the lower limbs, in particular the so-called "heavy leg" phenomenon, this is felt by subjects who have malfunctioning of the venous system and/or alteration in vascular permeability, triggered or aggravated by factors related to heredity, sedentary lifestyle, prolonged standing, exposure to heat, or tobacco or alcohol abuse. This phenomenon is characterised by a dilation of the veins, and is manifested by the appearance of pain, tingling and swelling of the calf, feet and ankles.

There therefore exists a need to have available satisfactory solutions for preventing or treating reductions in production of ATP by the endothelial cells under the effect of oxidising stress, so as to prevent and/or treat malfunctionings of the venous system and/or alteration in the vascular permeability that result in hypoxia of the endothelial cells of the human body and unaesthetic effects, such as for example periocular dark circles and/or bags and the phenomenon of "heavy legs".

Makeup products constitute a solution that makes it possible to mask or attenuate visible defects in the skin, and may present a solution to the presence of dark circles and bags in the periocular area. Foundations procure a matte appearance for the skin and unify the colour thereof. However, these cosmetic solutions make it possible to treat only the visible consequences of the malfunctionings of the venous system or alteration to the vascular permeability only on the periocular area without treating the causes thereof. Moreover, the use of these makeup compositions has the drawback of conferring on the skin a non-natural appearance and some of them are difficult to apply and may cause drying of the skin in the long term.

Another solution consists of promoting the production of nitric oxide by the mitochondria of the cells subject to the phenomenon of hypoxia. Nitric oxide is a known molecule that is released in particular by the endothelial cells, which causes the phenomenon of vasodilation and consequently an increase in the blood flow rate. The international publication WO 2008/141296 A1 describes a method for treating hypoxia of tissues in mammals by exposing said tissues to electromagnetic radiation in the visible part of the light spectrum, so as to promote the production of nitric oxide by the mitochondria of the tissues exposed to this radiation. The publication FR 2 883 171 A1 describes the use of agents promoting the production of nitric oxide in and/or on the skin, chosen from donors or precursors of nitric oxide, (such as for example compounds comprising nitro or nitroso substituents, oximes, hydroxylamine, N-hydroxy guanidine and salts thereof, nitrosilated transition metals, etc.), agents enabling the non-polymeric release of nitric oxide in the organism (such as for example amino acids, peptides), agents stimulating the synthesis and/or the activity of nitric oxide synthase (NOS) such as for example interleukins, lipopolysaccharides, L-glutamic acid or arachidonic acid. This approach through the implementation of solutions aimed at generating an increase in the production of nitric oxide in the organism does however have the drawbacks of concerning only the stimulation of the phenomenon of vasodilation and causing risks of deregulation of the vasodilation/vasoconstriction balance; the alternation and equilibrium of the two phenomena having to be respected in order to preserve and/or regain a functioning of the venous system and/or vascular permeability that are in balance.

Another solution consists of promoting the chelation of the $Fe^{3+}$ ions present in haemosiderin, which is a pigment resulting from the degradation of haemoglobin accumulated in the capillary vessels because of the slowing down in the blood microcirculation in the periocular region. The international publication WO 2008/035152 A1 describes several chelating agents for ferric ions that are effective and do not present any problems of ocular irritation when a formulation containing them is applied to the area to be preserved or treated.

These agents include: 3-hydroxy 2-methyl 4-pyrone (or maltol), ethyl maltol, oxtopirox, ciclopirox, rilopirox, gallic acid, gallic acid esters, kojic acid and derivatives of kojic acid. This solution, apart from the fact that it uses compounds either in a mixture with plant extracts or obtained at the end of multistep processes not suited to the cosmetics industry, make it possible to treat only the visible consequences of malfunctionings of the venous system or alteration to the vascular permeability solely on the periocular region without treating their causes.

Japanese patent application No 2000-229921 describes the use of polyol esters of N-acylamino acids as effective surfactants (paragraph [0003] of said application). The international publication WO 2010/034917 describes the monoesters and diesters of polyols of N-(ω-undecylenoyl) phenylalanine and uses thereof as agents for lightening the human skin.

European patent application No EP 0 839 515 A2 generically discloses N-acylamino acid esters and use thereof as an agent for promoting hair growth, as a moistening agent and as an agent for accelerating subcutaneous blood flow. The European patent application No EP 0 839 515 A2 more particularly discloses expressly an ethylene glycol ester of N-pentadecanoyl aspartate, as well as use thereof as an agent for promoting hair growth.

To our knowledge, no ester of N-acylamino acid derivatives and aliphatic diols has been described as being capable of preventing and/or treating reductions in production of ATP by the endothelial cells subjected to oxidising stress. Consequently, to our knowledge, no ester of N-acylamino acid derivatives and aliphatic diols has been described as being capable of preventing and/or treating malfunctionings of the venous system and/or alteration to vascular permeability.

Likewise, to our knowledge, no ester of N-acyl amino acid derivatives and aliphatic diols has been described as being capable of preventing the appearance of and/or reducing the unaesthetic effects caused by hypoxia of endothelial cells of the human body, such as for example periocular dark circles and/or bags and the phenomenon of "heavy legs".

The applicant has therefore set out to develop a novel technical solution consisting of novel esters of N-acyl derivatives of amino acids and aliphatic diols, which prevent and/or slow down the reduction in the production of ATP by endothelial cells subjected to oxidising stresses, so as to prevent and/or treat malfunctionings of the venous system and/or alteration in vascular permeability, and consequently to prevent the appearance and/or to reduce the unaesthetic effects caused by hypoxia of endothelial cells of the human body, such as for example periocular dark circles and/or bags and the phenomenon of "heavy legs".

This is why, according to a first aspect, the subject matter of the invention is a compound of formula (I):

R'—O-A-O—R"  (I)

formula (I) in which R' and R", identical or different, represent:
either a hydrogen atom;
or a monovalent radical of formula (IIa)

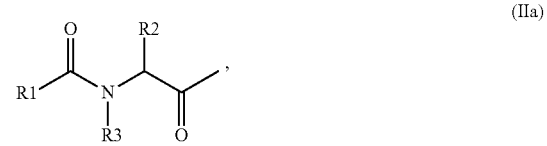

(IIa)

in which:
R1 represents an aliphatic radical, saturated or unsaturated, linear or branched, comprising 7 to 30 carbon atoms,
R2 represents a hydrogen atom or a radical chosen from the following radicals: methyl, isopropyl, isobutyl, 1-methyl propyl, hydroxymethyl, 1-hydroxy ethyl, thiomethyl, 2-methylthio ethyl, 4-aminobutyl, 3-guanidino propyl, 3-ureido propyl, (1-amino carbonyl)methyl, 2-(amino carbonyl)ethyl, benzyl, 4-hydroxy benzyl, 3,4-dihydroxy benzyl, [1H-indol-3-yl]methyl, (1H-imidazol-4-yl)methyl, 3-amino propyl, and R3 represents a hydrogen atom or a methyl radical;
or a monovalent radical of formula (IIb):

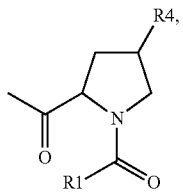
(IIb)

in which:
R1 is as defined in formula (IIa) and
R4 represents a hydrogen atom or a hydroxy radical, it being understood that at least one of the radicals R' or R" is not a hydrogen atom and that, when none of the radicals R' and R" is a hydrogen atom, R' and R" are identical, and formula (I) in which A represents the divalent radical of formula (III):

—CH(X1)-[C(X2)(X3)]p-CH(X4)-      (III)

in which:
X1, X2, X3 and X4, identical or different, are either a hydrogen atom, or a methyl radical, or an ethyl radical, and
p is an integer number greater than or equal to 1 and less than or equal to 6.

According to a particular aspect, in the definition of the radical of formula (IIa) or of the radical of formula (IIb), the radical $R_1$—C(=O)— represents a radical chosen from the following radicals: octanoyl, decanoyl, ω-undecylenoyl, dodecanoyl, tetradecanoyl, hexadecanoyl, octadecanoyl, eicosanoyl, docasanoyl, 9-octadecenoyl, eicosenoyl, 13-docosenoyl, 9,12-octadecadienoyl or 9,12,15-octadecatrienoyl.

According to another particular aspect of the present invention, the subject matter of the latter is a compound of formula (I) as defined previously, in which the radicals R' and R", identical or different, are:
either a hydrogen atom;
or a monovalent radical of formula (IIa), in which R1 and R3 are as defined previously and R2 is a radical chosen from the methyl, isopropyl, isobutyl, 1-methyl propyl or benzyl radicals,
or a monovalent radical of formula (IIb), in which R1 is as defined previously and R4 is a hydrogen atom.

According to this particular aspect of the present invention, the compound of formula (I) as defined above is more particularly chosen from the esters derived from the following amino acids: alanine, valine, proline, leucine, phenylalanine, isoleucine.

According to another particular aspect of the present invention, the subject matter of the latter is a compound of formula (I) as defined previously, in which A represents the divalent radical of formula (IIIa):

—CH$_2$)$_q$—      (IIIa)

in which q is equal to 3, 4 or 6, corresponding to formula (III) in which X1, X2, X3 and X4 are identical and each represent a hydrogen atom, and p represents an integer equal to 1, 2 or 4.

According to this particular aspect of the present invention, the compound of formula (I) as defined above is then chosen from the esters of 1,3-propanediol when p is an integer number equal to 1, the esters of 1,4-butanediol when p is an integer number equal to 2, the esters of 1,6-hexanediol when p is an integer number equal to 4.

According to this particular aspect of the present invention, the compound of formula (I) as defined above A represents more particularly the divalent radical —(CH$_2$)$_3$—.

According to another particular aspect of the present invention, the subject matter of the latter is a compound of formula (I) as defined previously, in which X1, X2 and X3 are identical are a hydrogen atom, X4 is an aliphatic radical selected from the methyl, ethyl, propyl, butyl, pentyl, hexyl, heptyl, octyl, nonyl and decyl radicals, and p is an integer number equal to 1 in the definition of formula (III) of the divalent radical A.

According to this particular aspect of the present invention, the compound of formula (I) is characterised in that A represents the divalent radical —(CH$_2$)$_2$—CH(CH$_3$)—.

According to another particular aspect, the subject matter of the invention is a compound of formula (Ia):

R'—O-A-O—H      (Ia), corresponding to formula (I) as defined previously, in which R" is a hydrogen atom, and more particularly one of the following compounds:

the compound of formula (Ia11):

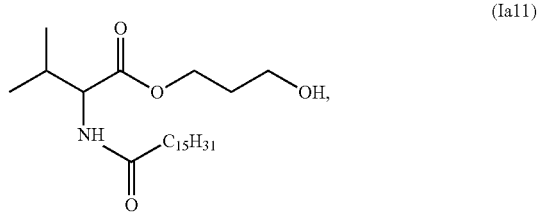
(Ia11)

the compound of formula (Ia12):

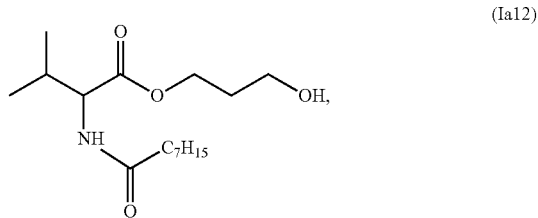
(Ia12)

the compound of formula (Ia13):

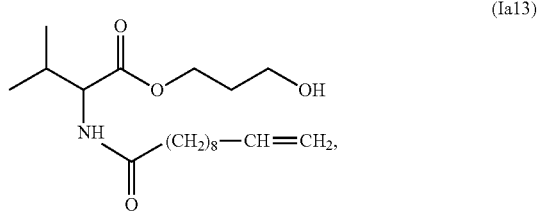
(Ia13)

the compound of formula (Ia14):

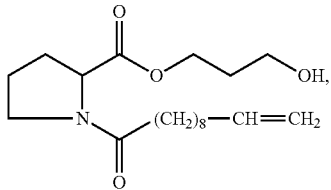

the compound of formula (Ia15):

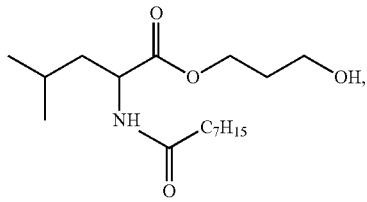

the compound of formula (Ia21):

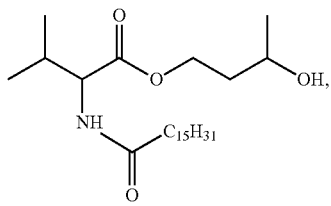

the compound of formula (Ia22):

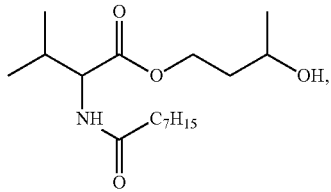

the compound of formula (Ia23):

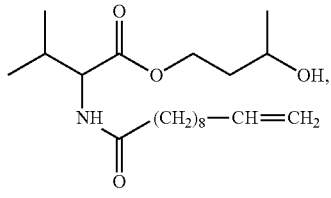

the compound of formula (Ia24):

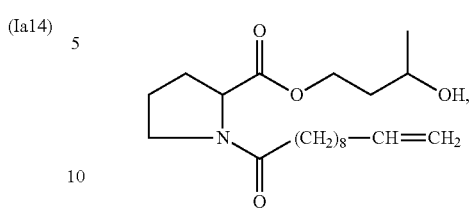

the compound of formula (Ia25):

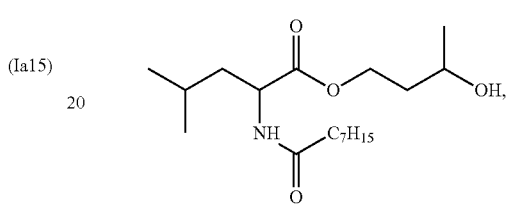

the compound of formula (Ia31):

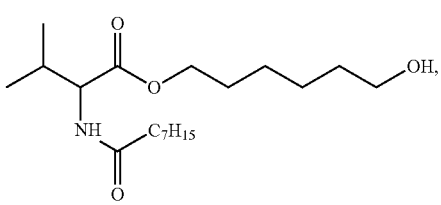

the compound of formula (Ia32):

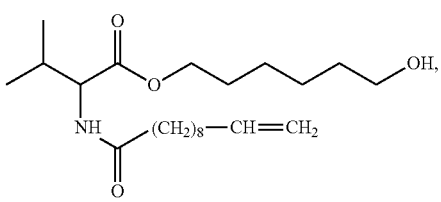

the compound of formula (Ia33):

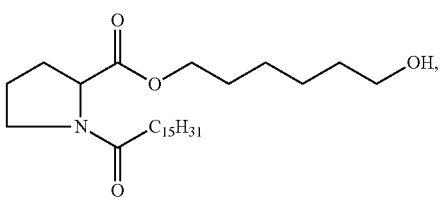

According to this particular aspect of the present invention, the compounds of formulae (Ia11), (Ia12), (Ia13), (Ia14) and (Ia15) are more particularly respectively chosen from the following compounds:

1,3 propanediol mono N-hexadecanoyl valinate,
1,3 propanediol mono N-octanoyl valinate,
1,3 propanediol mono N-(ω-undecylenoyl) valinate,
1,3 propanediol mono N-(ω-undecylenoyl) prolinate,
1,3 propanediol mono N-octanoyl leucinate.

According to this particular aspect of the present invention, the compounds of formulae (Ia21), (Ia22), (Ia23), (Ia24) and (Ia25) are more particularly respectively chosen from:
1,3 butanediol mono N-hexadecanoyl valinate,
1,3 butanediol mono N-octanoyl valinate,
1,3 butanediol mono N-(ω-undecylenoyl) valinate,
1,3 butanediol mono N-(ω-undecylenoyl) prolinate,
1,3 butanediol mono N-octanoyl leucinate.

According to this particular aspect of the present invention, the compounds of formulae (Ia31), (Ia32) and (Ia33) are more particularly respectively chosen from:
1,6 hexanediol mono N-octanoyl valinate.
1,6 hexanediol mono N-(ω-undecylenoyl) valinate,
1,6 hexanediol mono N-hexadecanoyl prolinate, According to another particular aspect, the subject matter of the invention is a compound of formula (Ib):

R—O-A-O—R     (Ib)

corresponding to formula (I) as defined previously, in which the radicals R' and R" are identical, and are represented by the radical R, and more particularly one of the following compounds:

the compound of formula (Ib11):

the compound of formula (Ib12):

the compound of formula (Ib13):

the compound of formula (Ib14):

the compound of formula (Ib15):

the compound of formula (Ib21):

the compound of formula (Ib22):

the compound of formula (Ib23):

the compound of formula (Ib24):

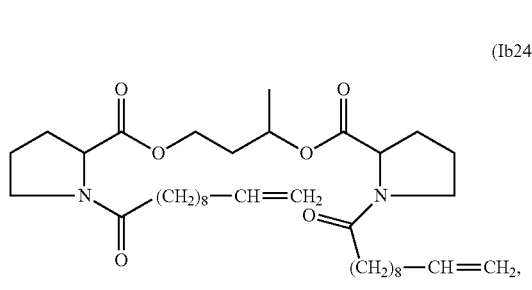

the compound of formula (Ib25):

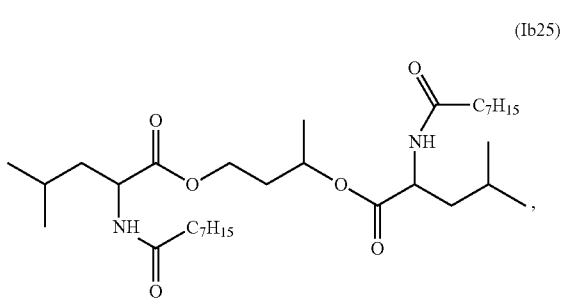

the compound of formula (Ib31):

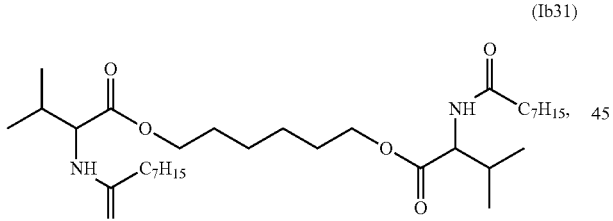

the compound of formula (Ib32):

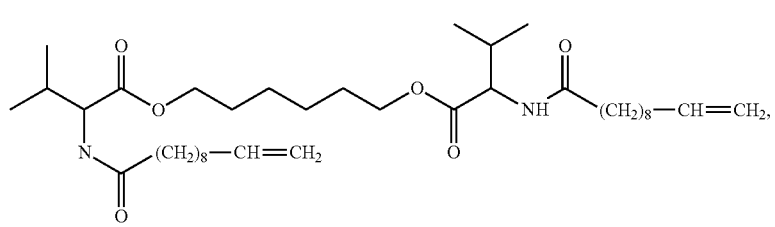

the compound of formula (Ib33):

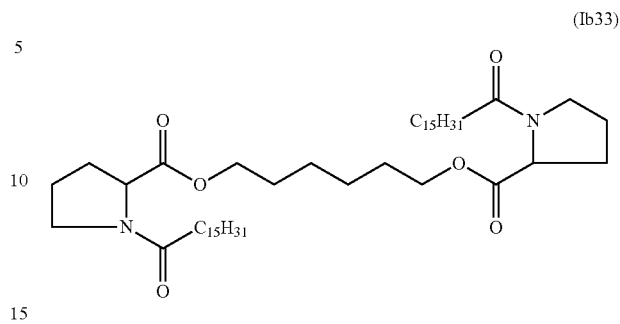

According to this particular aspect of the present invention, the compounds of formulae (Ib11), (Ib12), (Ib13), (Ib14) and (Ib15) are more particularly respectively chosen from:
1,3 propanediol di N-hexadecanoyl valinate,
1,3 propanediol di N-octanoyl valinate,
1,3 propanediol di N-(ω-undecylenoyl) valinate,
1,3 propanediol di N-(ω-undecylenoyl) prolinate,
1,3 propanediol di N-octanoyl leucinate.

According to this particular aspect of the present invention, the compounds of formulae (Ib21), (Ib22), (Ib23), (Ib24) and (Ib25) are more particularly respectively chosen from:
1,3 propanediol di N-hexadecanoyl valinate,
1,3 propanediol di N-octanoyl valinate,
1,3 propanediol di N-(ω-undecylenoyl) valinate,
1,3 propanediol di N-(ω-undecylenoyl) prolinate,
1,3 propanediol di N-octanoyl leucinate.

According to this particular aspect of the present invention, the compounds of formulae (Ib31), (Ib32), and (Ib33) are more particularly respectively chosen from:
1,6 hexanediol di N-octanoyl valinate.
1,6 hexanediol di N-(ω-undecylenoyl) valinate,
1,6 hexanediol di N-hexadecanoyl prolinate.

Another subject matter of the invention is a method for preparing a compound of formula (I) as defined previously comprising:
a step a) of esterification:
either of a compound of formula (IVa):

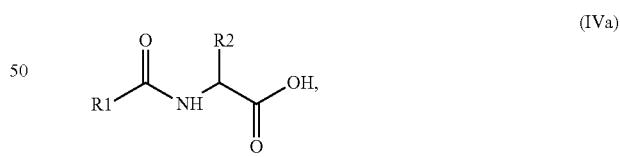

in which R1 and R2 are as defined in formula (IIa),
or a compound of formula (IVb):

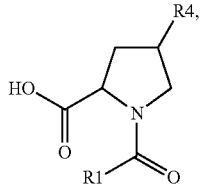
(IVb)

in which R1 and R4 are as defined in formula (IIb),
with the compound of formula (V)

H—O-A-O—H    (V)

in which A is a divalent radical of formula (III) as defined previously,
in order to obtain either the compound of formula (Ia) or the compound of formula (Ib) or a mixture (M) of the compound of formula (Ia) and the compound of formula (Ib); and, if necessary or if desired, a step b) of separating the compounds of formula (Ia) and formula (Ib), from said mixture (M) obtained at step (a).

The compounds of formulae (IVa) and IVb) are known or can be synthesised by N-acylation of the corresponding α-amino acids according to methods known to persons skilled in the art.

In the method that is the subject matter of the present invention as defined above, step a) is generally performed at a temperature of between approximately 80° C. and 180° C., and particularly between 100° C. and 150° C., even more particularly between 120° C. and 150° C., under inert gas, and in the presence of an acidic catalytic system. Acidic catalytic system means strong acids such as sulphuric acid, hydrochloric acid, phosphoric acid, nitric acid, hypophosphorous acid, methanesulfonic acid, para-toluene sulfonic acid, trifluoromethane sulfonic acid, or acidic ion exchange resins.

In the method as defined above, the molar ratio of compound of formula (IVa) or formula (IVb) to compound of formula (V) is generally between 3/1 and 1/5, more particularly between 1/1 and 1.5, and even more particularly between 1.1 and 1.3.

In the method as defined above, step b) of separation of the compound of formula (Ia) and formula (Ib) is performed by the conventional separation methods known to persons skilled in the art.

Another subject matter of the invention is a variant of the preparation method as defined above, comprising:

a step a1) of esterfication either of the compound of formula (IVa) as defined previously, or of the compound of formula (IVb) as defined previously, with an alcohol of formula (VI):

R5-OH    (VI)

in which R5 is a linear aliphatic radical comprising 1 to 4 carbon atoms, in order to form:

either a compound of formula (VIIa):

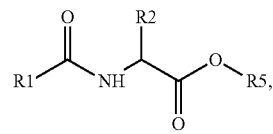
(VIIa)

in which R1, R2 and R5 are as defined previously,
or a compound of formula (VIIb):

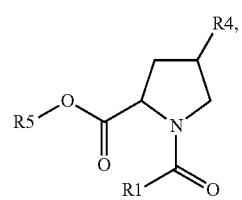
(VIIb)

in which R1, R4 and R5 are as defined previously:

a step a2) of transesterfication of the compound of formula (VIIa) or of the compound of formula (VIIb) obtained at step a1), by reaction with the compound of formula (V), in order to obtain either the compound of formula (Ia) or the compound (Ib), or a mixture (M) of the compound of formula (Ia) and the compound of formula (Ib); and, if necessary or if desired, implementation of step b).

In the variant of the method that is the subject matter of the present invention as defined above, step a1) is generally performed at a temperature of between approximately 60° C. and 120° C., under inert gas, and in the presence of an acidic catalytic system. Acidic catalytic system means strong acids such as sulphuric acid, hydrochloric acid, phosphoric acid, nitric acid, hypophosphorous acid, methanesulfonic acid, para-toluene sulfonic acid, trifluoromethane sulfonic acid or acid ion exchange resins.

In step a1) of the variant of the method that is the subject matter of the present invention as defined above, the molar ratio of the compound of formula (IVa) or formula (IVb) to the alcohol of formula (VI) is generally between 1/1 and 1/10, more particularly between 1/1 and 1/8 or even more particularly between 1/2 and 1/8.

In the variant of the method that is the subject matter of the present invention as defined above, step a2) of transesterification of the ester of formula (VIIIa) and/or of formula (VIIb) obtained at step a1) is generally performed at a temperature of between approximately 80° C. and 180° C., more particularly between 100° C. and 150° C., even more particularly between 120° C. and 150° C., under inert gas, and in the presence of an acidic catalytic system as described above, with distillation under vacuum of the alcohol of formula (VI) formed in situ.

In step a2) of this variant, the molar ratio of the compound of formula (VIIa) and/or formula (VIIb) to the compound of formula (V) is between 3/1 and 1/5, more particularly between 1/1 and 1/5, and even more particularly between 1/1 and 1/3.

Another subject matter of the invention is a composition (C1) comprising, for 100% of its mass:

from 99% by mass to 20% by mass of at least one compound of formula (Ia) as defined previously; and
from 1% by mass to 80% by mass of at least one compound of formula (Ib) as defined previously.

According to a particular aspect, in the composition (C1) that is the subject matter of the present invention, compound (Ia) is selected from the compounds of formula (Ia11), (Ia12), (Ia13), (Ia14), (Ia15), (Ia21), (Ia22), (Ia23), (Ia24) or (Ia25) as defined previously and compound (Ib) is selected from the compounds of formula (Ib11), (Ib12), (Ib13), (Ib14), (Ib15), (Ib21), (Ib22), (Ib23), (Ib24) or (Ib25) as defined previously.

The composition (C1) that is the subject matter of the invention can be prepared by various methods.

A first method for preparing the composition (C1) that is the subject matter of the invention consists of mixing, in the required proportions by mass, the compound of formula (Ia) as defined above or the mixture of compounds of formula (Ia), with the compound of formula (Ib) as defined above, or the mixture of compounds of formula (Ib).

A second method for preparing the composition (C1) that is the subject matter of the invention consists of implementing the method for preparing the compound of formula (I) as described previously, by reacting, in the required proportions, the compound of formula (V) with the compound of formula (IVa) or of formula (IVb) or a mixture of compounds of formula (IVa) and formula (IVb).

A third method for preparing the composition (C1) that is the subject matter of the present invention consists of implementing the variant of the method for preparing the compound of formula (I) as described previously, by reacting, in the required proportions, the compound of formula (V) with the compound of formula (VIIa) or formula (VIIb) or a mixture of compounds of formula (VIIa) and formula (VIIb).

Another subject matter of the invention is the use of the compound of formula (I) or of the composition (C1) as defined previously, as a cosmetic active agent, for preventing and/or limiting the unaesthetic effects caused by hypoxia of the endothelial cells of the human body and more particularly those caused by periocular dark circles or bags and/or heavy legs.

The compound of formula (I) and the composition (C1) that are the subjects of the present invention may be administered orally, topically or parenterally.

Another subject matter of the invention is a cosmetic formulation for topical use characterised in that it comprises at least one cosmetically acceptable excipient and an effective quantity of the compound of formula (I) or of the composition (C1) as defined previously.

The expression "for topical use" used in the definition of the cosmetic formulation as described above means that said formulation is used by application on the skin, whether it be a case of a direct application in the case of a cosmetic formulation or an indirect application for example in the case of a body care product in the form of a textile or paper wipe or sanitary products intended to be in contact with the skin.

The expression "cosmetically acceptable" used in the definition of the cosmetic formulation as described above means, according to the directive of the Council of the European Economic Community N° 76/768/CEE of 27 Jul. 1976 as amended by directive N° 93/35/CEE of 14 Jun. 1993, that the formulation comprises any substance or preparation intended to be put in contact with the various parts of the human body (epidermis, hair or pilous system, nails, lips and genital organs) or with the teeth and the mouth mucosa with a view, solely and mainly, to cleansing them, to perfuming them, to modifying the appearance thereof and/or to correcting body odours thereof and/or to protecting or keeping them in good condition.

Another subject matter of the invention is a method for the non-therapeutic treatment of the human skin intended to prevent the appearance of and/or to reduce periocular dark circles and/or bags and/or the phenomenon of heavy legs, comprising at least one step of applying to said human skin an effective quantity of the cosmetic formulation for topical use as defined above.

Effective quantity of the compound of formula (I) as defined previously or of a composition (C1) as defined previously, present in the cosmetic formulation for topical use as defined previously, intended to prevent and/or limit the unaesthetic effects caused by the hypoxia of endothelial cells of the human body and more particularly those caused by periocular dark circles or bags and/or heavy legs, means, for 100% of the mass of said cosmetic formulation for topical use, the quantity lying between 0.1% and 5% by mass, more particularly between 0.1% and 3% by mass, and even more particularly between 0.5% and 2% by mass of compound of formula (I) or of composition (C1).

In the non-therapeutic treatment method as described above, the cosmetic formulation for topical use is spread over the surface of the skin to be treated, and then the skin is massaged for a few moments.

The cosmetic formulation for topical use that is the subject matter of the present invention is generally in the form of dilute aqueous or water/alcohol solutions, in the form of single or multiple emulsions, such as water in oil (W/O), oil in water (O/W) or water in oil in water (W/O/W) emulsions, in which the oil is of a plant or mineral nature, or in powder form. They may also be dispersed or impregnated on textile or on non-woven materials, whether it be wipes, paper towels or garments.

In general terms, the compound of formula (I) or the composition (C1) is associated with numerous types of adjuvants or active ingredients used in the cosmetic formulation as defined above and which is the subject matter of the present invention, whether it be a case of fats, organic solvents, thickeners, gelling agents, softeners, foaming surfactants and/or detergents, superfatting agents, thickening and/or gelling surfactants, antioxidants, opacifiers, stabilisers, foaming agents, perfumes, emulsifying surfactants, hydrotropic agents, plasticers, superfatting agents, texture agents, pigments, sequestring agents, chelating agents, preservatives, essential oils, dyes, hydrophilic or lipophilic active agents, moisteners, perfumes, mineral or organic sun filters, mineral fillers, or any other ingredient normally used in cosmetics.

Examples of oils that can be associated with the compound of formula (I) or composition (C1) in the cosmetic formulations for topical use that are the subject matter of the present invention include mineral oils such as paraffin oil, vaseline oil, isoparaffins or mineral white oils, oils of animal origin such as squalene or squalane, vegetable oils such as sweet almond oil, coprah oil, castor oil, jojoba oil, olive oil, rapeseed oil, ground nut oil, sunflower oil, wheatgerm oil, maize germ oil, soya oil, cotton oil, alfalfa oil, poppy oil, pumpkin oil, evening primrose oil, millet oil, barley oil, rye oil, safflower oil, candleberry oil, passion flower oil, hazelnut oil, palm oil, shea butter, apricot kernel oil, calophyllum oil, sysymbrium oil, avocado oil, calendula oil; ethoxylated plant oils; synthetic oils such as fatty acid esters such as butyl myristate, propyl myristate, cetyl myristate, isopropyl palmitate, butyle stearate, hexadecyl stearate, isopropyl stearate, octyl stearate, isocetyl stearate, dodecyl oleate, hexyl laurate, propyleneglycol dicaprylate, ester derivatives of lanolic acid, such as isopropyl lanolate, isocetyl lanolate, monglycerides, diglycerides and triglycerides of fatty acids such as glycerol triheptonoate, alkylbenzoates, polyalfaolenfins, polyolefins such as polyisobutene, synthesis isoalkane, such as isohexadecane, isododecane, perfluorinated oils and silicone oils. The latter include more particularly dimethylpolysiloxanes, methylphenylpolysiloxanes, silicones modified by amines, silicones modified by fatty acids, silicones modified by alcohols, silicones modified by alcohols and fatty acids, silicones modified by polyether groups, modified epoxy silicones, silicones modified by fluorinated groups, cyclic silicones and silicones modified by alkyl groups.

Other fats that can be associated with the compound of formula (I) or composition (C1) in cosmetic formulations for topical use that are the subjects of the present invention include fatty alcohols and fatty acids.

Examples of waxes that can be associated with the compound of formula (I) or composition (C1) in the cosmetic formulations for topical use that are the subjects of the present invention include for example beeswax; carnauba wax; candelilla wax; ouricoury wax; Japan wax; cork fibre wax or sugarcane wax; paraffin waxes, lignite waxes; microcristalline waxes; lanolin wax; ozocerite; polyethylene wax; hydrogenated oils; silicone waxes; vegetable waxes; fatty alcohols and fatty acids solid at ambient temperature; glycerides solid at ambient temperature.

Examples of thickening and/or emulsifying polymers that can be associated with the compound of formula (I) or composition (C1) in the cosmetic formulations for topical use that are the subject matter of the present invention include homopolymers, or copolymers of acrylic acid or derivatives of acrylic acid, homopolymers or copolymers of acrylamide, homopolymers or copolymers of acrylamide derivatives, homopolymers or copolymers of acrylamido methylpropane sulfonic acid, vinyl monomer, trimethylaminoethyl acrylate chloride, hydrocolloids of plant or biosynthetic origin, for example xanthan gum, karaya gum, carraghenates, alginates; silicates; cellulose and derivatives thereof; starch and hydrophylic derivatives thereof; polyurethanes.

Polymers of the polyelectrolyte type that can be associated with the compound of formula (I) or composition ($C_1$) in the cosmetic formulations for topical use that are the subject matter of the present invention include for example copolymers of acrylic acid and 2-methyl-[(1-oxo-2-propenyl)amino]1-propane sulfonic acid (MPSA), copolymers of acrylamine and 2-methyl-[(1-oxo-2-propenyl)amino]1-propane sulfonic acid, copolymers of 2-methyl-[(1-oxo-2-propenyl)amino]1-propane sulfonic acid and (2-hydroxyethyl)acrylate, the homopolymer of 2-methyl-[(1-oxo-2-propenyl)amino]1-propane sulfonic acid, the homopolymer of acrylic acid, the copolymers of acryloyl ethyl trimethyl ammonium chloride and acrylamide, the copolymers of MPSA and vinylpyrolidone, the copolymers of acrylic acid and alkyl acrylates the carbon chain of which comprises between ten and thirty carbon atoms, the copolymers of MPSA and alkyl acrylates the carbon chain of which comprises between ten and thirty carbon atoms. Such polymers are sold respectively under the names SIMULGEL™ EG, SEPIGEL™ 305, SIMULGEL™ NS, SIMULGEL™ 800 and SIMULGEL™ A by the applicant.

Examples of emulsifiers that can be associated with the compound of formula (I) or composition (C1) in the cosmetic formulations for topical use that are the subject matter of the present invention include fatty acids, ethyloxated fatty acids, esters of fatty acid and sorbitol, esters of ethyloxated fatty acids, polysorbates, polyglycerol esters, ethyloxated fatty alcohols, sucrose esters, alkylpolyglycosides, sulfated and phosphated fatty alcohols or the mixtures of alkylpolyglycosides and fatty alcohols described in the French patent applications 2 668 080, 2 734 496, 2 756 195, 2 762 317, 2 784 680, 2 784 904, 2 791 565, 2 790 977, 2 807 435 and 2 804 432.

Examples of foaming surfactants and/or detergents that can be associated with the compound of formula (I) or composition (C1) in the cosmetic formulations for topical use that are the subject matter of the present invention include: the topically acceptable anionic, cationic, amphoteric or non-ionic surfactants normally used in this field of activity.

The anionic surfactants that can be associated with the compound of formula (I) or composition (C1) in the cosmetic formulations for topical use that are the subject matter of the present invention include particularly alkaline metal salts, alkaline earth metal salts, ammonium salts, amine salts, the aminoalcohol salts of the following compounds: alkylether sulfates, alkyl sulfates, alkylamidoether sulfates, alkylarylpolyether sulfates, monoglyderide sulfates, alphaolefin sulfates, paraffin sulfonates, alkyl phosphates, alkylether phosphates, alkyl sulfonates, alkylamide sulfonates, alkylaryl sulfonates, alkylcarboxylates, alkylsulfosuccinates, alkylethersulfosuccinates, alkylamidesulfosuccinates, alkylsulfoacetates, alkylsarcosinates, acylated thionates, N-acyltaurates and acyllactates.

The anionic surfactants that can be associated with the compound of formula (I) or composition (C1) in the cosmetic formulations for topical use that are the subject matter of the present invention also include the N-acylated derivatives of amino acids, peptides, proteins the acyl chain of which comprises 8 to 16 carbon atoms; fatty acid salts, acid salts of coprah oil, optionally hydrogenated.

The amphoteric surfactants that can be associated with the compound of formula (I) of composition (C1) in the cosmetic formulations for topical use that are the subject matter of the present invention include particularly alkybetaines, alkylamidobetaines, sultaines, alkylamidoalkylsulfobetaines, imidazoline derivaties, phosphobetaines, amphopolyacetates and amphoprionates.

The cationic surfactants that can be associated with the compound of formula (I) or composition (C1) in the cosmetic formulations for topical use that are the subject matter of the present invention include particularly the quaternary ammonium derivatives.

The non-ionic surfactants that can be associated with the compound of formula (I) or composition (C1) in the cosmetic formulations for topical use that are the subject matter of the present invention include particularly the alkylpolyglycosides the alkyle chain of which comprises 8 to 16 carbon atoms, castor oil derivatives, polysorbates, coprah amides, N-alkylamines and amine oxides.

Examples of texture agents that can be associated with the compound of formula (I) or composition (C1) in the cosmetic formulations for topical use that are the subject matter of the present invention include for example N-acylated derivatives of amino acids, such as for example the lauroyl lysine sold under the name AMINOHOPE™ LL by the company AJINOMOTO, the octenyl starch succinates sold under the name DRYFLO™ by the company NATIONAL STARCH, the myristyl polyglucoside sold by SEPPIC under the name MONTANOV 14, cellulose fibres, cotton fibres, chitosan fibres, talc, sericite or mica.

Examples of opacifiers and/or pearling agents that can be associated with the compound of formula (I) or composition (C1) in the cosmetic formulations for topical use that are the subject matter of the present invention include sodium palmitate, sodium stearate, sodium hydroxystearate, magnesium palmitate, magnesium stearate, magnesium hydroxystearate, ethylene glycol monstearate, ethylene glycol distearate, polyethylene glycol monostearate, polyethylene glycol distearate and fatty alcohols.

Examples of thickening and/or gelling surfactants that can be associated with the compound of formula (I) or composition (C1) in the cosmetic formulations for topical use that are the subject matter of the present invention include:

fatty esters of alkylpolyglycosides, optionally alkoxylated, and especially ethoxylated methylpolyglucoside esters such as PEG 120 methyl glucose trioleate and PEG 120 methyl glucose dioleate sold respectively under the names GLUCAMATE™ LT and GLUMATE™ DOE120;

alkoxylated fatty esters such as PEG 150 pentaerythrytyl tetrasterate sold under the name CROTHIX™ DS53, PEG 55 propylene glycol oleate sold under the name ANTIL™ 141;

fatty-chain polyalkylene glycol carbamates such as PPG 14 laureth isophoryl dicarbamate sold under the name EFLACOS™ T211, PPG 14 palmeth 60 hexyl dicarbamate sold under the name ELFACOS™ GT2125.

Examples of sun filters that can be associated with the compound of formula (I) or composition (C1) in the cosmetic formulations for topical use that are the subject matter of the present invention include all those appearing in the amended cosmetic directive 76/768/EEC appendix VII.

Examples of active ingredients that can associated with the compound of formula (I) or composition (C1) in the cosmetic formulations for topical use that are the subject matter of the present invention include the compounds having a lightening or depigmenting action such as for example arbutin, kojic acid, hydroquinone, ellagic acid, vitamin C, magnesium ascorbyl phosphate, extracts of polyphenols, derivatives of glycosylated polyphenols such as Rosmarinyl glucoside, grape extracts, pine extracts, wine extracts, extracts of olives, pond extracts, N-acylated proteins, N-acylated peptides, N-acylated amino acids, partial hydrolysates of N-acylated proteins, amino acids, peptides, total hydrolysates of proteins, partial hydrolysates of proteins, polyols (for example glycerine or butylene glycol), urea, pyrrolidone carboxylic acid or derivatives of this acid, glycyrrhetinic acid, alpha-bisabolol, sugars or derivatives of sugars, polysaccharides or derives thereof, hydroxyacids, for example lactic acid, vitamins, vitamin derivatives such as Retinol, vitamin E and derivatives thereof, minerals, enzymes, co-enzymes such as co-enzyme Q10, hormones or hormone-like substances, soya extracts, for example Raffermine™, wheat extracts, for example Tensine™ or Gliadine™, plant extracts such as tanin-rich extracts, isoflavone-rich extracts or terpene-rich extracts, extracts of fresh or seawater algae, essential waxes, bacterial extracts, minerals, lipids in general, lipids such as ceramides or phospholipids, active agents having a slimming action such as caffeine or derivatives thereof, such as quinoa extracts sold under the name ADIPOLESS™, such as the Canadian hemlock extract sold under the name SERENIKS™ 207, such as the composition comprising Lauroyl Proline sold under the name ADIPOSLIM™, the active agents having an antimicrobial activity or purifying action vis-à-vis oily skins such as LIPACIDE™ PVB, active agents having an energising or stimulating property such as SEPITONIC™ M3 or Physiogenyl™, panthenol and derivatives thereof such as SEPICAP™ MP, anti-aging active agents such as SEPILIFT™ DPHP, LIPICIDE™ PVB, SEPIVINOL™, SEPIVITAL™, hydrating active agents such as SEPICALM™ S, SEPICALM™ VG and SEPILIFT™ DPHP, "anti-photo aging" anti-aging active agents, active agents protecting the integrity of the dermo-epidermal junction, active agents increasing the synthesis of components of the extracellular matrix, active agents having a slimming activity such as caffeine, theophylline, AMPc, green tea, sage, ginko biloba, ivy, horse chesnut, bamboo, ruscus, butcher's broom, centella asiatica, heather, ulmaria, fucus, rosemary, willow, active agents creating a "heating" sensation on the skin such as skin microcirculation activators (for example nicotinates) or products creating a sensation of "coolness" on the skin (for example menthol and derivatives thereof).

Another subject matter of the invention is a compound of formula (I) or a composition (C1) as defined previously, for implementing a method for the therapeutic treatment of the human or animal body and more particularly a compound of formula (I) or a composition (C1) as defined previously, for use thereof in a method for the therapeutic treatment of hypoxia of the endothelial cells of the human or animal body, and more particularly a method for the therapeutic treatment of periocular dark circles or bags and/or heavy legs.

The following experimental study illustrates the invention without however limiting same.

EXAMPLES OF PREPARATION OF COMPOUNDS OF FORMULA (I) ACCORDING TO THE INVENTION

Example 1

Preparation of a Composition A1 Comprising the Compounds of Formulae (Ia21) and (Ib21)

239 grams of valine, that is to say a molar equivalent, is introduced into a mixture of 2161 grams consisting of 1512 grams of water and 649 grams of isopropanol included in a double-jacket glass reactor, in which a heat-transfer fluid is circulating, provided with effective agitation and a device for nitrogen bubbling through the bottom of the reactor, at a temperature of 20° C. The pH of the medium thus prepared is adjusted to a pH value of 10 by adding a 30% soda solution. 450 grams of hexadecanoyl chloride, that is to say 0.8 molar equivalents, is then added gradually to the medium at a temperature of between 20° C. and 30° C., so as to control the exothermic reaction; a 30% soda solution is added at the same time to the medium so as to maintain the pH of the medium at between 10 and 10.5.

At the end of the addition of the hexadecanoyl chloride, the reaction medium is kept under agitation for a period of 2 hours. The reaction medium is then raised to a temperature of 55° C. under agitation and a quantity of 469 grams of a 75% acidic solution of phosphoric acid is then gradually introduced so as to obtain a pH of the reaction medium of around 2.0. The agitation is stopped and the aqueous phase of the settled medium is then drawn off. The organic phase remaining in the reactor is then washed with a quantity of 2700 grams of a 10% aqueous solution of sodium chloride at a temperature of 60° C. under agitation. The aqueous phase is drawn off through the bottom of the reactor and the washing phase as described previously is repeated an additional time. At the end of the washing, the organic phase is dried by distillation of the residual water under vacuum.

A quantity of 32 grams of 1,3-butanediol, that is to say a molar equivalent, is introduced into the reactor comprising 126 grams of the reaction medium dried, agitated and raised to a temperature of 120° C. When the mixture is dispersed, a quantity of 0.4 grams of 98% sulphuric acid is introduced into the reactor, and the resulting mixture is raised to a temperature of 120° C., under partial vacuum with a regular bubbling of nitrogen introduced through the bottom of the reactor. The reaction mixture is then maintained for a period of 24 hours under agitation and at 120° C., and then neutralised by adding a 30% soda solution so as to obtain a pH of 5% of the reaction medium between 3.0 and 6.0. The reaction medium is then drained and the analytical characteristics of the composition A1 measured are as follows:
Acid number (according to NFT 60-204)=36.5
pH 5% of the composition A1 in water (according to the NFT 73-206 method)=7.1
Hydroxyl number (according to US Pharmacopeia XXI NF XVI 01/011985)=135.5
Ester number (saponification number (according to NFT 60-110)-acid index)=100.8

Example 2

Preparation of a Composition A2 Comprising the Compounds of Formulae (Ia11) and (Ib11)

The operating mode of the method described in example 1 is implemented for a molar equivalent of valine, 0.8 molar equivalent of hexadecanoyl chloride and a molar equivalent of 1,3-propanediol in order to obtain the composition A2, the analytical characteristics of which are as follows:
Acid number (according to NFT 60-204)=28.3
pH 5% of the composition A2 in water (according to the NFT 73-206 method)=6.7
Hydroxyl number (according to US Pharmacopeia XXI NF XVI 01/011985)=80.5
Ester number (saponification number (according to NFT 60-110)-acid index)=121.7

Example 3

Preparation of a Composition B1 Comprising the Compounds of Formulae (Ia22) and (Ib22)

The operating mode of the method described in example 1 is implemented for a molar equivalent of valine, 0.8 molar equivalent of octanoyl chloride and a molar equivalent of 1,3-butanediol in order to obtain the composition B1, the analytical characteristics of which are as follows:
Acid number (according to NFT 60-204)=55.7
pH 5% of the composition B1 in water (according to the NFT 73-206 method)=4.2
Hydroxyl number (according to US Pharmacopeia XXI NF XVI 01/011985)=194.6
Ester number (saponification number (according to NFT 60-110)-acid index)=128.2

Example 4

Preparation of a Composition B2 Comprising the Compounds of Formulae (Ia12) and (Ib12)

The operating mode of the method described in example 1 is implemented for a molar equivalent of valine, 0.8 molar equivalent of octanoyl chloride and a molar equivalent of 1,3-propanediol in order to obtain the composition B2, the analytical characteristics of which are as follows:
Acid number (according to NFT 60-204)=54.2
pH 5% of the composition B2 in water (according to the NFT 73-206 method)=4.5
Hydroxyl number (according to US Pharmacopeia XXI NF XVI 01/011985)=21.2
Ester number (saponification number (according to NFT 60-110)-acid index)=159.0

Example 5

Preparation of a Composition D1 Comprising the Compounds of Formulae (Ia23) and (Ib23)

The operating mode of the method described in example 1 is implemented for a molar equivalent of valine, 0.8 molar equivalent of undecylenoyl chloride and a molar equivalent of 1,3-butanediol in order to obtain the composition D1, the analytical characteristics of which are as follows:
Acid number (according to NFT 60-204)=50.0
pH 5% of the composition D1 in water (according to the NFT 73-206 method)=5.3
Hydroxyl number (according to US Pharmacopeia XXI NF XVI 01/011985)=149.9
Ester number (saponification number (according to NFT 60-110)-acid index)=114.0

Example 6

Preparation of a Composition D2 Comprising the Compounds of Formulae (Ia13) and (Ib13)

The operating mode of the method described in example 1 is implemented for a molar equivalent of valine, 0.8 molar equivalent of undecylenoyl chloride and a molar equivalent of 1,3-propanediol in order to obtain the composition D2, the analytical characteristics of which are as follows:
Acid number (according to NFT 60-204)=38.6
pH 5% of the composition D2 in water (according to the NFT 73-206 method)=5.7
Hydroxyl number (according to US Pharmacopeia XXI NF XVI 01/011985)=189.7
Ester number (saponification number (according to NFT 60-110)-acid index)=135.1

Example 7

Preparation of a Composition E1 Comprising the Compounds of Formulae (Ia24) and (Ib24)

The operating mode of the method described in example 1 is implemented for a molar equivalent of proline, 0.8 molar equivalent of undecylenoyl chloride and a molar equivalent of 1,3-propanediol in order to obtain the composition E1, the analytical characteristics of which are as follows:
Acid number (according to NFT 60-204)=41.9
pH 5% of the composition E1 in water (according to the NFT 73-206 method)=5.0
Hydroxyl number (according to US Pharmacopeia XXI NF XVI 01/011985)=142.6
Ester number (saponification number (according to NFT 60-110)-acid index)=116.0

Example 8

Preparation of a Composition E2 Comprising the Compounds of Formulae (Ia14) and (Ib14)

The operating mode of the method described in example 1 is implemented for a molar equivalent of porline, 0.8 molar equivalent of undecylenoyl chloride and a molar equivalent of 1,3-propanediol in order to obtain the composition E2, the analytical characteristics of which are as follows:
Acid number (according to NFT 60-204)=25.6
pH 5% of the composition E2 in water (according to the NFT 73-206 method)=5.3
Hydroxyl number (according to US Pharmacopeia XXI NF XVI 01/011985)=149.7
Ester number (saponification number (according to NFT 60-110)-acid index)=152.2

Example 9

Preparation of a Composition F1 Comprising the Compounds of Formulae (Ia25) and (Ib25)

The operating mode of the method described in example 1 is implemented for a molar equivalent of leucine, 0.8 molar equivalent of octanoyl chloride and a molar equivalent of 1,3-propanediol in order to obtain the composition F1, the analytical characteristics of which are as follows:
Acid number (according to NFT 60-204)=27.1
pH 5% of the composition F1 in water (according to the NFT 73-206 method)=5.3
Hydroxyl number (according to US Pharmacopeia XXI NF XVI 01/011985)=99.9
Ester number (saponification number (according to NFT 60-110)-acid index)=169.4
Evaluation of the Effect of Compounds and Compositions According to the Invention on the Production of Intracellular ATP in Enthothelial Cell Cultures Having Undergone Oxidising Stress
Protocol Passage R3 HUVEC (Human Umbilical Vein Endothethial Cells) are seeded at 2000 cells/well in plates comprising 96 wells.

The cells are next cultivated in an EGM-2 (Endothelial Growth Medium), marketed by the company Lonza, for 7 days at a temperature of 37° C. under 5% $CO_2$.

The culture media are then replaced by EGM-2 medium, containing the dilutions of the compounds and compositions to be tested.

References (T) are also prepared by replacing culture media by the single EGM-2 medium.

The cells present in the EGM-2 medium and associated with the dilutions of the compounds and compositions to be tested, as well as the references (T), are then incubated for a period of 24 hours at a temperature of 37° C.

Following this incubation, the media of the cells associated with the dilutions of the compounds and compositions to be tested and the media of the references (T) are replaced by an EGM-2 medium supplemented with hydrogen peroxide at a concentration of 0.8 millimoles per liter.

"References (T1)" will hereinafter refer to the media of the references (T) supplemented with hydrogen peroxide and "references (T)" will refer to the media of the references (T) not supplemented with hydrogen peroxide.

The cells associated with the dilutions of the compounds and compositions to be tested, the references (T) and the references (T1) are next incubated for 10 minutes at a temperature of 37° C. and the rinsed with PBS (Phosphate Buffer Saline).

The quantity of intracellular ATP and the quantity of proteins produced by the cells associated with the dilutions of the compounds and compositions to be tested, the references (T) and the references (T1) are evaluated after lysis of the molecular carpets in the presence of a lysis buffer.

The quantity of ATP is quantified by the luminometric method, implemented by means of a luminometer plate reader of FLUOROSKAN ASCENT FL™ make sold by the company LABSYSTEMS, and the proteins are quantified by means of the BCA method. The latter method makes it possible to standardise the quantities of ATP dosed and to evaluate the cytotoxicity of each experimental condition.

A cytotoxicity threshold was fixed at 80% of the reference group.

The results are expressed in millimoles of ATP produced per milligram of proteins produced and the statistical study of the results was carried out by means of the bilateral Student's t-test with unequal variance.

The effects evaluated on the cells associated with the dilutions of the compounds and the compositions to be tested, the references (T) and the references (T1) were implemented on two independent experiments and the results presented correspond to the mean of the two tests.

For each experimental condition, the most restrictive statistics were applied. The results obtained are set out in the following table 1:

TABLE 1 evaluation of the effect of compositions A1, A2, B1, B2, D1, D2, E1, E2 and F1 on the production of ATP by HUVEC cells subjected to hydrogen peroxide.

| Composition tested | Concentration (% w/v with respect to the dry extract) | Quantity of ATP produced (mmoles of ATP/mg of proteins) |
| --- | --- | --- |
| Reference (T) | — | 0.045 |
| Reference (T1) | — | 0.016 |
| Composition A1 | 0.00075 | 0.029 |
| Composition A2 | 0.0005 | 0.020 |
| Composition B1 | 0.0005 | 0.021 |
| Composition B2 | 0.0005 | 0.021 |
| Composition D1 | 0.00005 | 0.020 |
| Composition D2 | 0.00005 | 0.024 |
| Composition E1 | 0.00005 | 0.020 |
| Composition E2 | 0.00005 | 0.020 |
| Composition F1 | 0.0005 | 0.018 |

The oxidising stress procured by the addition of hydrogen peroxide to the reference cells (T) causes a reduction of 64% in the ATP produced by the endothelial cells (reference cells (T1)). This result thus validates the conditions of the experimental test used.

When the endothelial cells are associated with the composition (A1), the quantity of ATP produced by said endothelial cells is an increase of 81.25% with respect to the reference cells (T1) subjected to the same oxidising stress.

When the endothelial cells are associated with the composition (D2), the quantity of ATP produced by said endothelial cells is an increase of 50.0% with respect to the reference cells (T1) subjected to the same oxidising stress.

When the endothelial cells are associated with compositions (B1) and (B2), the quantity of ATP produced by said endothelial cells is an increase of 31.25% with respect to the reference cells (T1) subjected to the same oxidising stress.

When the endothelial cells are associated with the compositions (A2), (D1), (E1) and (E2), the quantity of ATP produced by said endothelial cells is an increase of 25.0% with respect with respect to the reference cells (T1) subjected to the same oxidising stress.

When the endothelial cells are associated with the composition (F1), the quantity of ATP produced by said endothelial cells is an increase 12.5% with respect with respect to the reference cells (T1) subjected to the same oxidising stress.

None of the compositions tested caused significant cytotoxicity according the BCA test used with the "BC-assay" kit sold by the company Interchim.

As a result the compositions according to the invention comprising the compounds according to the invention slow down the reduction in the production of ATP by endothelial cells subjected to oxidising stresses.

BIBLIOGRAPHICAL REFERENCES CITED IN THE DESCRIPTION (1) Chang et al "Aging and survival of cutaneous microvasculature", J. Invest Dermatol, 2002 May; 118(5):752-8.
(2) Chung et al "Differential effects of photoaging vs intrinsic aging on the vascularisation of human skin" Arch. Dermatol, 2002 November; 138(11):1437-42.
(3) Toyoda et al "Ultrastructural characterisation of microvasculature in photoaging" J. Dematol Sci. 2001 August; 27 Supp 1:S32-41.
(4) Janssens, "Effect of venotropic drugs on the respiratory activity of isolated mitochondria and in endothelial cells", in British Journal of Pharmacology (2000) 130, 1513-1524.

The invention claimed is:

1. A compound of formula (I):

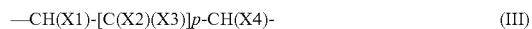  (I)

formula (I) wherein:
R' and R", identical or different, are each selected from the group consisting of:
(i) a hydrogen atom;
(ii) a monovalent radical of formula (IIa):

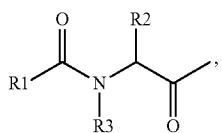  (IIa)

in which:
R1 represents an aliphatic radical, saturated or unsaturated, linear or branched, comprising 7 to 30 carbon atoms,
R2 represents a hydrogen atom or a radical selected from the group consisting of: methyl, isopropyl, isobutyl, 1-methyl propyl, hydroxymethyl, 1-hydroxy ethyl, thiomethyl, 2-methylthio ethyl, 4-aminobutyl, 3-guanidino propyl, 3-ureido propyl, (1-amino carbonyl) methyl, 2-(amino carbonyl) ethyl, benzyl, 4-hydroxy benzyl, 3,4-dihydroxy benzyl, [1H-indol-3-yl]methyl, (1H-imidazol-4-yl) methyl, and 3-amino propyl, and
R3 represents a hydrogen atom; and
(iii) a monovalent radical of formula (IIb):

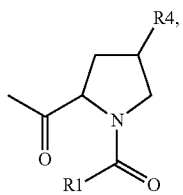  (IIb)

in which:
R1 is as defined in formula (IIa) and
R4 represents a hydrogen atom or a hydroxy radical, wherein at least one of the radicals R' or R" is not a hydrogen atom and, when none of the radicals R' and R" is a hydrogen atom, R' and R" are identical, and
A represents the divalent radical of formula (III):

—CH(X1)-[C(X2)(X3)]p-CH(X4)—  (III)

in which:
X1, X2, X3 and X4, identical or different, are either a hydrogen atom, or a methyl radical, or an ethyl radical, and
p is an integer number greater than or equal to 1 and less than or equal to 6.

2. The compound of formula (I) as defined in claim 1, for which, in formulae (IIa) and (IIb), the radical R1-C(=O)— represents a radical selected from the group consisting of: octanoyl, decanoyl, co-undecylenoyl, dodecanoyl, tetradecanoyl, hexadecanoyl, octadecanoyl, eicosenoyl, docasanoyl, 9-octadecenoyl, eicosenoyl, 13-docosenoyl, 9,12-octadecadienoyl and 9,12,15-octadecatrienoyl.

3. The compound of formula (I) as defined in claim 1, in which the radicals R' and R", identical or different, are selected from the group consisting of:
(i) a hydrogen atom;
(ii) a monovalent radical of formula (IIa), in which R1 and R3 are as defined previously and R2 is a radical selected from the group consisting of methyl, isopropyl, isobutyl, 1-methyl propyl or and benzyl; and
(iii) a monovalent radical of formula (IIb), in which R1 is as defined previously and R4 is a hydrogen atom.

4. The compound of formula (I) as defined in claim 1, in which A represents the divalent radical of formula (IIIa):

—CH$_2$)$_q$—  (IIIa)

in which q is equal to 3, 4 or 6, corresponding to formula (III) in which X1, X2, X3 and X4 are identical and each represent a hydrogen atom, and p represents an integer equal to 1, 2 or 4.

5. The compound of formula (I) as defined in claim 4, in which A represents the divalent radical:

—(CH$_2$)$_3$—.

6. The compound of formula (I) as defined in claim 1, in which A represents the divalent radical:

—(CH$_2$)$_2$—CH(CH$_3$)—.

7. The compound of formula (Ia):

R'—O-A-O—H  (Ia), corresponding to formula (I) as defined in claim 1, in which R" is a hydrogen atom.

8. The compound of formula (Ib):

R—O-A-O—R  (Ib)

corresponding to formula (I) as defined in claim 1, in which the radicals R' and R" are identical, and are represented by the radical R.

9. A method for preparing a compound of formula (I) as defined in claim 1, comprising:

a step a) of esterification:
either of a compound of formula (IVa):

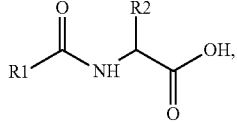

in which R1 and R2 are as defined in formula (IIa),
or a compound of formula (IVb):

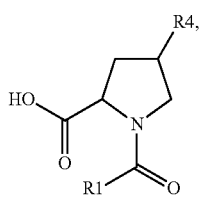

in which R1 and R4 are as defined in formula (IIb),
with the compound of formula (V)

      (V)

in which A is a divalent radical of formula (III) as defined previously,
in order to obtain either the compound of formula (Ia) or the compound of formula (Ib) or a mixture (M) of the compound of formula (Ia) and the compound of formula (Ib); and, optionally, a step b) of separating the compounds of formula (Ia) and formula (Ib), from said mixture (M) obtained at step (a).

10. The preparation method as defined in claim 1, comprising:

a step a1) of esterfication either of the compound of formula (IVa) as defined previously, or of the compound of formula (IVb) as defined previously, with an alcohol of formula (VI):

      (VI)

in which R5 is a linear aliphatic radical comprising 1 to 4 carbon atoms, in order to form:
either a compound of formula (VIIa):

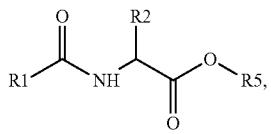

in which R1, R2 and R5 are as defined previously, or a compound of formula (VIIb):

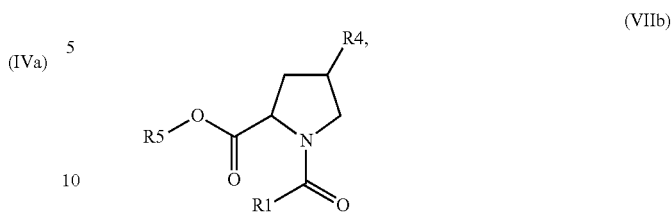

in which R1, R4 and R5 are as defined previously:

a step a2) of transesterfication of the compound of formula (VIIa) or of the compound of formula (VIIb) obtained at step a1, by reaction with the compound of formula (V), in order to obtain either the compound of formula (Ia) or the compound (Ib), or a mixture (M) of the compound of formula (Ia) and the compound of formula (Ib); and, optionally,
implementation of step b).

11. A composition (C1) comprising, for 100% mass of said composition:
from 99% by mass to 20% by mass of at least one compound of formula (Ia):

      (Ia)

corresponding to formula (I) as defined in claim 1, in which R" is a hydrogen atom; and
from 1% by mass to 80% by mass of at least one compound of formula (Ib):

      (Ib)

corresponding to formula (I) as defined in claim 1, in which the radicals R' and R" are identical, and are represented by the radical R.

12. A cosmetic formulation for topical use, comprising at least one cosmetically acceptable excipient and an effective quantity of the composition (C1) as defined in claim 11.

13. A method for the non-therapeutic treatment of the human skin intended to prevent the appearance of and/or to reduce periocular dark circles and/or bags and/or the phenomenon of heavy legs, comprising at least one step of applying to said human skin an effective quantity of the cosmetic formulation for topical use as defined in claim 12.

14. A method for the therapeutic treatment of hypoxia of the endothelial cells of the human or animal body, comprising administering to a subject in need thereof an effective amount of composition (C1) as defined in claim 11.

15. A cosmetic formulation for topical use, comprising at least one cosmetically acceptable excipient and an effective quantity of the compound of formula (I) as defined in claim 1.

16. A method for the non-therapeutic treatment of the human skin intended to prevent the appearance of and/or to reduce periocular dark circles and/or bags and/or the phenomenon of heavy legs, comprising at least one step of applying to said human skin an effective quantity of the cosmetic formulation for topical use as defined in claim 15.

17. A method for the therapeutic treatment of hypoxia of the endothelial cells of the human or animal body, comprising administering to a subject in need thereof an effective amount of a compound of formula (I) as defined in claim 1.

18. The method according to claim 14, wherein the therapeutic treatment of hypoxia of the endothelial cells of the human or animal body is the therapeutic treatment of peri-ocular dark circles or bags and/or heavy legs.

19. The method according to claim 17, wherein the therapeutic treatment of hypoxia of the endothelial cells of the human or animal body is the therapeutic treatment of peri-ocular dark circles or bags and/or heavy legs.

\* \* \* \* \*